United States Patent
Kaneumi et al.

(10) Patent No.: US 9,610,634 B2
(45) Date of Patent: Apr. 4, 2017

(54) EMULSION AND MOLD-RELEASING AGENT USING THE SAME

(75) Inventors: Yoshiyama Kaneumi, Ibaraki (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 1029 days.

(21) Appl. No.: 13/496,581

(22) PCT Filed: Sep. 10, 2010

(86) PCT No.: PCT/JP2010/065620
§ 371 (c)(1),
(2), (4) Date: Mar. 16, 2012

(87) PCT Pub. No.: WO2011/034003
PCT Pub. Date: Mar. 24, 2011

(65) Prior Publication Data
US 2012/0178075 A1    Jul. 12, 2012

(30) Foreign Application Priority Data

Sep. 17, 2009 (JP) ................. 2009-215238
Sep. 17, 2009 (JP) ................. 2009-215239

(51) Int. Cl.
*C09K 3/18* (2006.01)
*B22C 3/00* (2006.01)
(Continued)

(52) U.S. Cl.
CPC ............. *B22C 3/00* (2013.01); *A01N 1/021* (2013.01); *B29C 33/62* (2013.01); *C08G 65/007* (2013.01);
(Continued)

(58) Field of Classification Search
CPC ... A01N 1/021; B29C 33/62; B29K 2105/0064; C08G 65/007; C08G 65/3353; C08G 2650/48; C08L 71/00; C08K 5/5337
(Continued)

(56) References Cited

U.S. PATENT DOCUMENTS 4,118,235 A * 10/1978 Horiuchi ............... B28B 7/384
106/287.13
7,956,225 B2 * 6/2011 Sato et al. .................. 570/155
(Continued)

FOREIGN PATENT DOCUMENTS

JP     52-036588     3/1977
JP     52-039587     3/1977
(Continued)

OTHER PUBLICATIONS

JPO machine translation, Shiseido Co Ltd, JP 08-323187 A (Pat. Publ. date Dec. 10, 1996), JPO, Tokyo, Japan, Downloaded Jan. 2015) pp. 1-10.*
(Continued)

*Primary Examiner* — Daniel S Metzmaier
(74) *Attorney, Agent, or Firm* — Brinks Gilson & Lione

(57) ABSTRACT

Disclosed is an emulsion formed using, as an emulsifier, 0.01 to 30 parts by weight of a perfluoroalkylethyl phosphonic acid salt represented by the general formula: $C_nF_{2n+1}CH_2CH_2P(O)(OM^1)(OM^2)$ [III] ($M^1$: a hydrogen atom, ammonium salt, or organic amine salt, $M^2$: an ammonium salt or organic amine salt, n: 1 to 6), based on 100 parts by weight of a perfluoropolyether oil represented by the general formula: $RfO(C_3F_6O)_p(C_2F_4O)_q(CF_2O)_rRf'$ [I] (Rf and Rf': $C_1$-$C_5$ perfluoroalkyl groups, p+q+r: 2 to 200) or the general formula: $F(CF_2CF_2CF_2O)_nCF_2CF_3$ [II] (n: 2 to 100), or a perfluorocarbon compound. In spite of using, as an emulsifier, a compound having a perfluoroalkyl group containing 6 or less carbon atoms, which is said to have low bioaccumulation potential, the emulsion exhibits excellent
(Continued)

emulsification stability, and therefore can be effectively used as a surface-treating agent, such as a mold-releasing agent.

6 Claims, 1 Drawing Sheet

(51) Int. Cl.
    *B29C 33/62*     (2006.01)
    *C08G 65/00*     (2006.01)
    *A01N 1/02*     (2006.01)
    *C08G 65/335*     (2006.01)
    *C08L 71/00*     (2006.01)
    *B29K 105/00*     (2006.01)
    *C08K 5/5337*     (2006.01)

(52) U.S. Cl.
    CPC .......... *C08G 65/3353* (2013.01); *C08L 71/00* (2013.01); *B29K 2105/0064* (2013.01); *C08G 2650/48* (2013.01); *C08K 5/5337* (2013.01)

(58) Field of Classification Search
    USPC .......................................................... 516/56
    See application file for complete search history.

(56) References Cited

U.S. PATENT DOCUMENTS

| | | | | |
|---|---|---|---|---|
| 8,197,586 B2* | 6/2012 | Kaneumi et al. | ........ | 106/38.22 |
| 8,313,573 B2* | 11/2012 | Kaneumi et al. | ........ | 106/38.22 |
| 8,361,215 B2* | 1/2013 | Kaneumi et al. | ........ | 106/38.22 |
| 8,377,187 B2* | 2/2013 | Kaneumi et al. | ........ | 106/38.22 |
| 8,377,188 B2* | 2/2013 | Kaneumi et al. | ........ | 106/38.22 |
| 8,454,738 B2* | 6/2013 | Kaneumi et al. | ........ | 106/38.22 |
| 9,068,059 B2* | 6/2015 | Kaneumi | ........ | C08F 2/26 |
| 9,498,761 B2* | 11/2016 | Wilfong | ........ | B01F 17/0035 |
| 2015/0306659 A1* | 10/2015 | Kaneumi | ........ | B29C 33/62 |
| | | | | 106/38.22 |
| 2016/0243237 A1* | 8/2016 | Kiral | ........ | A01N 1/021 |

FOREIGN PATENT DOCUMENTS

| | | |
|---|---|---|
| JP | 55-133490 | 10/1980 |
| JP | 58-180597 | 10/1983 |
| JP | 58-210096 | 12/1983 |
| JP | 59-166596 | 9/1984 |
| JP | 60-190309 | 9/1985 |
| JP | 60-193615 | 10/1985 |
| JP | 01-285312 | 11/1989 |
| JP | 04-062113 | 2/1992 |
| JP | 04-218600 | 8/1992 |
| JP | 07-196401 | 8/1995 |
| JP | 08-323187 | 12/1996 |
| JP | 3018091 B2 * | 1/2000 |
| JP | 2000-072601 | 3/2000 |
| JP | 2001-072857 | 3/2001 |
| JP | 2003-286404 | 10/2003 |

OTHER PUBLICATIONS

PTO 97-2529, Translation of Japan Kokai 01-285312 (Mold-Release Agent), USPTO, Washington, D. C. (Apr. 1997), Translated by: Schreiber Translations, Inc., pp. 1-24.*

Machine Translation of Publ. No. JP 3018091, published Jan. 2000, Japan Patent Office, Tokyo, Japan, online at https://dossier1.j-platpat.inpit.go.jp/tri/all/odse/ODSE_GM101_Top.action (Downloaded Aug. 3, 2015), pp. 1-7.*

Hawley's Condensed Chemical Dictionary, (2007), 499, John Wiley & Sons, Inc. Online @ http://onlinelibrary.wiley.com/book/10.1002/9780470114735/titles headwords = Emulsion, (downloaded Jan. 9, 2016), pp. 1 of 1.*

International Preliminary Report on Patentability and Written Opinion from corresponding PCT application No. PCT/JP2010/065620 dated Apr. 19, 2012 (8 pgs).

International Search Report based on corresponding PCT application No. PCT/JP2010/065620 dated Dec. 7, 2010 (6 pgs).

* cited by examiner

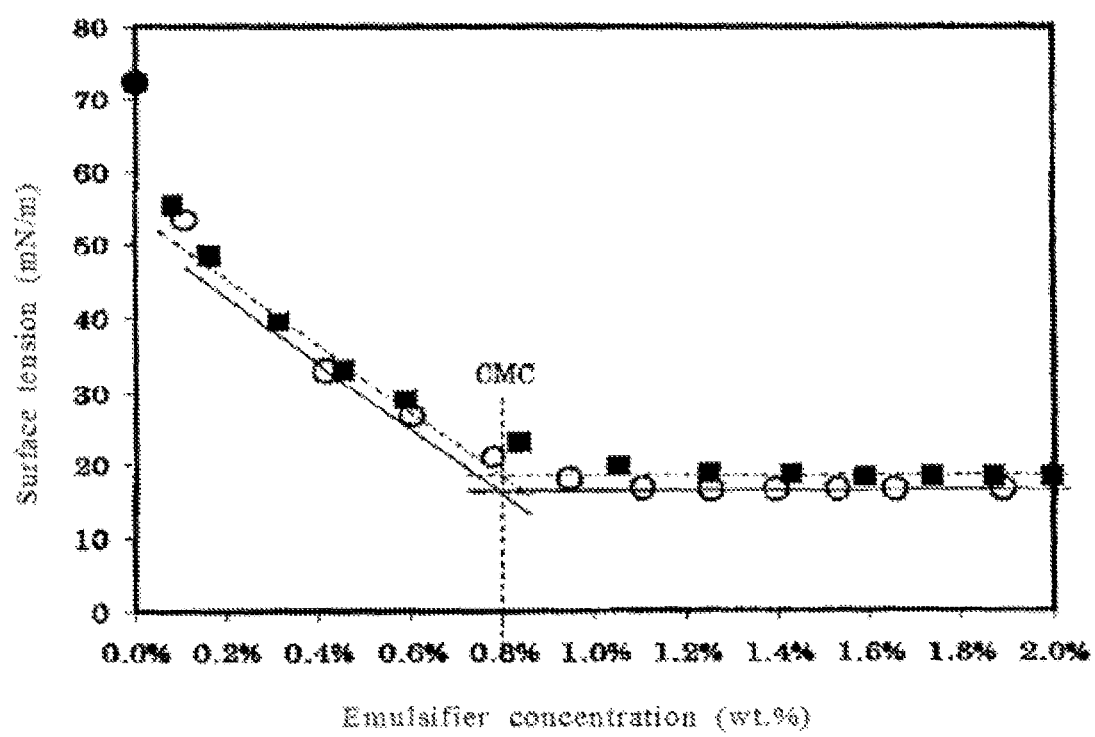

EMULSION AND MOLD-RELEASING AGENT USING THE SAME

RELATED APPLICATION

This application is a 35 U.S.C. §371 national phase filing of International Patent Application No. PCT/JP2010/065620, filed Sep. 10, 2010, through which and to which priority is claimed under 35 U.S.C. §119 to Japanese Patent Application Nos. 2009-215238, filed Sep. 17, 2009 and 2009-215239, filed Sep. 17, 2009, the entire disclosures of which are hereby expressly incorporated by reference.

TECHNICAL FIELD

The present invention relates to an emulsion and a mold-releasing agent using the same. More particularly, the present invention relates to an emulsion of a perfluoropolyether oil or perfluorocarbon compound, and a mold-releasing agent using the same.

BACKGROUND ART

Currently, silicone oil, wax, talc, mica, tetrafluoroethylene resin, and other mold-releasing agents are used in the molding of polymeric materials, such as plastic materials and rubber materials, using molds. Although silicone oil, wax, etc., have excellent mold releasability, such mold-releasing agents are transferred to molded products, thereby impairing the uniform coating properties, secondary processability, etc., of the molded products; in addition, durability is not sufficient. As for tetrafluoroethylene resin, the durability of mold release effect and secondary processability are satisfactory; however, it is necessary to perform bake treatment to form a film on the molding surface of a mold in the mold-release treatment, and the same treatment is required for retreating. Consequently, many treating processes are required.

In order to solve these defects, mold-releasing agents comprising a $C_4$-$C_{20}$ polyfluoroalkyl group-containing phosphoric acid ester as one of their active ingredients are proposed (see Patent Documents 1 to 3). These mold-releasing agents exhibit excellent mold releasability and have a longer mold release life than conventional mold-releasing agents; however, due to the recent trend toward the more complicated shape of molded products, there is a demand for mold-releasing agents having much higher performance.

Polyfluoroalkylethyl phosphonic acid esters are also widely used as starting materials for the synthesis of mold-releasing agents. Compounds having a $C_8$-$C_{12}$ perfluoroalkyl group are most likely to develop mold release performance when used as mold-releasing agents. In particular, phosphonate compounds having a perfluorooctyl group and represented by the formula:

are preferably used in this kind of application (see Patent Documents 4 to 7).

Incidentally, it is reported that telomer compounds having a $C_8$-$C_{12}$ perfluoroalkyl group are biologically degraded in the environment and converted to compounds having relatively high bioaccumulation and environmental concentration, causing concerns for exposure during treatment processes, and for release or diffusion from waste, treated substrates, etc., into the environment. Moreover, compounds having a perfluoroalkyl group containing 14 or more carbon atoms are very difficult to handle because of their physical and chemical properties, and hence, such compounds are rarely used in practice.

Furthermore, as for telomer compounds having a perfluoroalkyl group containing 8 or more carbon atoms, generation and mixing of perfluorooctanoic acids with high bioaccumulation potential is unavoidable during the production process of these compounds. For these reasons, companies that produce such telomer compounds have retreated from the production of the compounds or promoted the use of alternative compounds having a perfluoroalkyl group containing 6 or less carbon atoms.

However, compounds having a perfluoroalkyl group containing 6 or less carbon atoms cause a significant decrease in orientation on the surface of a treated substrate, and the melting point, glass transition point (Tg), etc., of the compounds are markedly lower than those of $C_8$ compounds. Accordingly, the compounds are highly influenced by their using environmental conditions, such as temperature, humidity, stress, and contact with organic solvents. Consequently, the desired performance cannot be sufficiently achieved, and durability and other properties are affected.

An aqueous mold-releasing agent composition in which an ammonium salt or amine salt of perfluoroalkylalkyl phosphonic acid and polyether-modified organopolysiloxane are dissolved or dispersed in water is also proposed (see Patent Document 8). Perfluorooctylethyl phosphonic acid salt is also used in this case, and a transparent mold releasing agent solution is obtained.

Moreover, perfluoropolyether oils widely used as water- and oil-repellents, lubricants, etc., have excellent water- and oil-repellency and lubricity; however, due to the lack of compatibility with other compounds, they have limited application.

There is an attempt to use a perfluoropolyether oil as a leather-treating agent by adding thereto a fat-liquoring agent (see Patent Document 9). In the general description, phosphonic acid derivatives having a fluoroalkyl group, fluoroalkenyl group, or fluoroether group, or ammonium salts, alkali metal salts, or alkaline earth metal salts thereof are referred to as examples of the fat-liquoring agent, and the fat-liquoring agent is used at a weight ratio of 10 to 0.5, preferably 5 to 1, relative to the fluorine-based oil.

Patent Document 9 indicates that the fluorine oil and fat-liquoring agent used at such a weight ratio are generally used as a leather-treating agent contained in the form of emulsion, and the leather-treating agent is used to treat tanned leather in the fat-liquoring process. As for the treating agent rich in the fat-liquoring agent, the average particle diameter of the emulsion is lower in proportion to the amount of emulsifier used, and stability over time is ensured; however, because of the excessive content of the hydrophilic fat-liquoring agent, the material to be treated becomes hydrophilic to reduce water-repellency. Further, when this is used as a mold-releasing agent, reduction of mold releasability is unavoidable (see Comparative Example 3, described later).

The present applicant has previously proposed a method for producing perfluoroalkylethyl phosphonic acid by pyrolysis or hydrolysis of perfluoroalkylethyl phosphonic acid diester (see Patent Document 10). The perfluoroalkylethyl phosphonic acid obtained by this method is not dissolved in an aqueous medium, such as water, and therefore cannot be used as an emulsifier aqueous solution, etc.

On the other hand, perfluoropolyether oils can be used as surface-treating agents by forming them into emulsions, and can be applied to mold-releasing agents.

However, although emulsions as described in Patent Document 9, in which an excessive amount of fat-liquoring agent (ammonium salt or metal salt of perfluoroalkylalkyl phosphonic acid) is mixed with fluorine-based oil, the emulsions can be suitably used in a leather treatment method, when the perfluoropolyether oil emulsion is applied as a mold-releasing agent, the mold releasability of these compounds themselves is not sufficiently exhibited.

PRIOR ART DOCUMENT

Patent Document

Patent Document 1: JP-B-53-23270
Patent Document 2: JP-B-53-23271
Patent Document 3: JP-B-57-48035
Patent Document 4: JP-B-2-45572
Patent Document 5: JP-B-3-78244
Patent Document 6: JP-B-4-4923
Patent Document 7: JP-B-4-11366
Patent Document 8: JP-B-8-5063
Patent Document 9: JP-B-3077231
Patent Document 10: JP-A-58-210096
Patent Document 11: JP-A-2000-72601

OUTLINE OF THE INVENTION

Problem to be Solved by the Invention

An object of the present invention is to provide an emulsion of a perfluoropolyether oil or perfluorocarbon compound using, as an emulsifier, a compound having a perfluoroalkyl group containing 6 or less carbon atoms, which is said to have low bioaccumulation potential, and having emulsification performance equivalent to the excellent emulsification performance of pentadecafluorooctanoic acid ammonium; and to provide a mold-releasing agent using the perfluoropolyether oil emulsion.

Means for Solving the Problem

The above object of the present invention can be accomplished by an emulsion formed using, as an emulsifier, 0.01 to 30 parts by weight of a perfluoroalkylethyl phosphonic acid represented by the general formula:

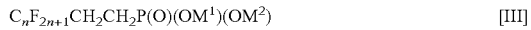

$C_nF_{2n+1}CH_2CH_2P(O)(OM^1)(OM^2)$     [III]

wherein $M^1$ is a hydrogen atom, ammonium salt, or organic amine salt, $M^2$ is an ammonium salt or organic amine salt, and n is an integer of 1 to 6, based on 100 parts by weight of a perfluoropolyether oil represented by the general formula:

$RfO(C_3F_6O)_p(C_2F_4O)_q(CF_2O)_rRf'$     [I]

wherein Rf and Rf' are perfluoro-lower alkyl groups having 1 to 5 carbon atoms, $C_3F_6O$ group, $C_2F_4O$ group, and $CF_2O$ group are bonded randomly, p+q+r is an integer of 2 to 200, and p, q, or r may be 0, or the general formula:

$F(CF_2CF_2CF_2O)_nCF_2CF_3$     [II]

wherein n is an integer of 2 to 100, or a perfluorocarbon compound. The object of the present invention can also be accomplished by a mold-releasing agent using the perfluoropolyether oil emulsion.

Effect of the Invention

The perfluoroalkylethyl phosphonic acid ammonium salt or amine salt emulsifier, particularly ammonium salt emulsifier, used in the present invention is a compound having a perfluoroalkyl group containing 6 or less carbon atoms, which is said to have low bioaccumulation potential, and having emulsification performance equivalent to the excellent emulsification performance of pentadecafluorooctanoic acid ammonium. An emulsion formed using an aqueous solution or organic solvent solution of the emulsifier and a perfluoropolyether oil or perfluorocarbon compound is stable. The emulsification stability of the emulsion is maintained at an excellent level even after being left for one month at room temperature or 40° C.

The emulsion with a perfluoropolyether oil can be suitably used for surface-treating agents, such as water- and oil-repellents, anti-adhesion agents, transfer inhibitors, and mold-releasing agents, while maintaining excellent emulsification stability. When used as a surface-treating agent of pigment powder for cosmetic powder, such as foundation, the emulsion is used as a water- and oil-repellency-imparting agent, transfer inhibitor, etc., of the pigment powder. Moreover, perfluorocarbon compounds can dissolve and carry a large amount of oxygen; therefore, the emulsion of the perfluorocarbon compound can be effectively used as an oxygen transport medium or organ storage solution.

Particularly for use in mold-releasing agents, for example, when the emulsion is prepared as an aqueous or organic solvent mold-releasing agent having a solid matters content of about 0.1 wt. % or less, the mold-releasing agent exhibits effective mold releasability when applied to an object to be subjected to mold release (e.g., a molding mold). This excellent effect is attributable to the extremely excellent solubility of the perfluoroalkylethyl phosphonic acid salt in solvents. A mold-releasing agent whose mold releasability is much more excellent than conventional mold-releasing agents prepared to have a solid matters content of 0.5 wt. %, can be obtained with a solid matters content of about 0.1 wt. % or less.

Moreover, the excellent solubility of the perfluoroalkylethyl phosphonic acid salt in solvents facilitates the formation of a mold-releasing agent solution with uniform concentration when the perfluoroalkylethyl phosphonic acid salt is diluted with a diluent. Accordingly, precipitation problematically formed in conventional mold-releasing agents does not occur, and good storage stability is ensured.

Owing to the above-described various properties of the perfluoroalkylethyl phosphonic acid salt, the emulsion-type mold-releasing agent of the present invention exhibits the following excellent effects:

(1) Film-forming properties are excellent, allowing the formation of uniform coating on molded products of a complicated shape.

(2) The film-forming properties of the mold-releasing agent for the mold surface and adhesion to the mold surface due to ionic groups are excellent, thereby significantly improving mold releasability and more release life.

(3) Mold releasability and durability are excellent even after dilution to low concentration (e.g., about 0.1 wt. %), reducing mold contamination caused by the mold-releasing agent.

(4) Since the transmission of the mold-releasing agent to the molded product is low, the quality of the molded product after molding in less adversely affected, improving the dimensional accuracy of the molded product.

BRIEF DESCRIPTION OF DRAWING

FIG. 1 is a graph showing the relationship between the emulsifier concentration and surface tension obtained in Example 1 (1) and Reference Example 1.

DESCRIPTION OF EMBODIMENTS

The perfluoroalkylethyl phosphonic acid salt represented by the formula:

$$C_nF_{2n+1}CH_2CH_2P(O)(OM^1)(OM^2) \quad [III]$$

used as an emulsifier is obtained by reacting the perfluoroalkylethyl phosphonic acid represented by the formula:

$$C_nF_{2n+1}CH_2CH_2P(O)(OH)_2 \quad [IV]$$

described in Patent Document 10, with an aqueous ammonia solution or organic amine.

As the organic amine, for example, diethylamine, triethylamine, diethanolamine, triethanolamine, pyridine, morpholine, or a derivative thereof is preferably used. The ammonia or organic amine forms mono-salts when used in an amount equimolar to the perfluoroalkylethyl phosphonic acid, and forms di-salts when used in an amount of two times the mole of the perfluoroalkylethyl phosphonic acid. Generally, the ammonia or organic amine is used in an amount not less than the theoretically required number of moles. When the ammonia or organic amine is used in an amount equimolar or more and less than two times the mole of the perfluoroalkylethyl phosphonic acid, a mixture of monosalts and di-salts is formed.

The perfluoroalkylethyl phosphonic acid salt is used as an aqueous solution in which the salt is dissolved in an aqueous medium (water or a water-soluble organic solvent aqueous solution), or as an organic solvent solution in which the salt is dissolved in an organic solvent. Examples of the organic solvent include alcohols, such as methanol, ethanol, and isopropanol; ketones, such as acetone, methyl ethyl ketone, and methyl isobutyl ketone; and aprotic polar solvents, such as acetonitrile, dimethylformamide, diethylformamide, dimethylacetamide, and N-methyl-2-pyrrolidone.

As for the emulsification ability of the perfluoroalkylethyl phosphonic acid salt, in the case of, for example, a 2-(perfluorohexyl)ethyl phosphonic acid ammonium aqueous solution, the critical micelle concentration [CMC] of the solution appears at an emulsifier concentration of about 0.8 wt. %, and the solution has constant low surface tension at an emulsifier concentration up to about 2.0 wt. %.

The aqueous solution or organic solvent solution of the emulsifier is added to the perfluoropolyether oil so that the active ingredient amount thereof is about 0.01 to 30 parts by weight, preferably about 0.1 to 15 parts by weight, based on 100 parts by weight of perfluoropolyether oil. The mixture is then subjected to an emulsification treatment to form a perfluoropolyether oil emulsion. When the emulsifier is used in an amount greater than this range, the perfluoropolyether oil cannot sufficiently exhibit its properties. The emulsification treatment is performed in such a manner that preliminary emulsification is carried out using a homogenizer, etc., at a rotational speed of about 500 to 10,000 rpm, and emulsification is further carried out using a high-pressure homogenizer at a pressure of about 100 to 800 kgf/cm² (about 9.8 to 78.4 MPa).

As the perfluoropolyether oil to be emulsified, one represented by the general formula:

$$RfO(C_3F_6O)_p(C_2F_4O)_q(CF_2O)_rRf' \quad [I]$$

is used. In this formula, Rf and Rf' are perfluoro-lower alkyl groups having 1 to 5 carbon atoms (e.g., perfluoromethyl groups and perfluoroethyl groups), $C_3F_6O$ group, $C_2F_4O$ group, and $CF_2O$ group are bonded randomly, p+q+r is 2 to 200, and p, q, or r may be 0. Specific examples of the perfluoropolyether oil represented by the above general formula are as follows.

$$RfO[CF(CF_3)CF_2O]mRf' \quad [Ia]$$

In this formula, m is 2 to 200. This perfluoropolyether oil is obtained by complete fluorination of a precursor produced by photooxidation polymerization of hexafluoropropene. Alternatively, this oil is obtained by anionic polymerization of hexafluoropropene oxide in the presence of a cesium fluoride catalyst, and fluorine-gas treatment of the obtained acid fluoride compound having a terminal-$CF(CF_3)COF$ group.

$$RfO[CF(CF_3)CF_2O]m(CF_2O)nRf' \quad [Ib]$$

In this formula, $CF(CF_3)CF_2O$ group and $CF_2O$ group are bonded randomly, m+n is 3 to 200, and m:n is (10:90) to (90:10). This perfluoropolyether oil is obtained by complete fluorination of a precursor produced by photooxidation polymerization of hexafluoropropene.

$$RfO(CF_2CF_2O)m(CF_2O)nRf' \quad [Ic]$$

In this formula, m+n is 3 to 200, and m:n is (10:90) to (90:10). This perfluoropolyether oil is obtained by complete fluorination of a precursor produced by photooxidation polymerization of tetrafluoroethylene.

Perfluoropolyether oils other than those represented by the above general formulae can also be used. For example, the following perfluoropolyether oil can be used.

$$F(CF_2CF_2CF_2O)nCF_2CF_3 \quad [II]$$

In this formula, n is 2 to 100. This perfluoropolyether oil is obtained by anionic polymerization of 2,2,3,3-tetrafluorooxetane in the presence of a cesium fluoride catalyst, and fluorine-gas treatment of the obtained fluorine-containing polyether $(CH_2CF_2CF_2O)n$ under ultraviolet irradiation at 160 to 300° C.

These perfluoropolyether oils listed as specific examples can be used singly or in combination; however, in terms of cost performance, the perfluoropolyether oil [Ia] or [Ib], particularly the perfluoropolyether oil [Ia], is preferably used. A usable example of the perfluoropolyether oil [Ia] is one in which m is an integer of 2 to 100, and the number average molecular weight (Mn) is about 300 to 50,000, preferably about 500 to 20,000.

The kinetic viscosity of these perfluoropolyether oils is not limited; however, those having a kinetic viscosity of 5 to 2,000 mm²/s (40° C.) are used as lubricants. In terms of use under high temperature conditions, those having a kinetic viscosity of 100 to 1,500 mm²/s (40° C.) are preferably used. More specifically, perfluoropolyether oils having a kinematic viscosity of about 5 mm²/s or less are largely evaporated, and do not comply with the requirements for the standard of JIS ball-and-roller bearing grease, class 3 specified as heat-resistant grease (i.e., the amount of evaporation is 1.5% or less). Conversely, perfluoropolyether oils having a kinematic viscosity of 2,000 mm²/s or more have a pour point (according to JIS K2283 corresponding to ISO 2909 and ISO 3104) of 10° C. or more; bearings cannot be rotated by an ordinary method at the time of low-temperature starting; and they must be heated to make them usable.

Moreover, the perfluoropolyether oil emulsion is used as an aqueous solution or organic solvent solution in which the emulsion is further diluted with an aqueous solution or organic solvent so as to have a solid matters (perfluoropolyether oil) content of about 0.01 to 30 wt. %, preferably about 0.05 to 10 wt. %, thereby forming a surface-treating agent, such as water- and oil-repellent, anti-adhesion agent, transfer inhibitor, or mold-releasing agent, while maintaining excellent emulsification stability. When the emulsion is used as a mold-releasing agent, the agent is applied to the surface of a molding mold. When applied on a substrate, such as a molded product, the emulsion is used as an anti-adhesion agent. Furthermore, when used in cosmetic powder, such as foundation, the emulsion is used as a water- and oil-repellency-imparting agent, a transfer inhibitor, etc. of pigment powder.

When used as a mold-releasing agent, the emulsion is diluted with water or an organic solvent. The organic solvent used is at least one of alcohols, such as methanol, ethanol, n-propanol, and isopropanol; ketones, such as acetone, methyl ethyl ketone, and methyl isobutyl ketone; ethers, such as diethyl ether, diisopropyl ether, dioxane, and tetrahydrofuran; esters, such as ethyl acetate and butyl acetate; polyvalent alcohol derivatives, such as methyl cellosolve, ethyl cellosolve, methyl carbitol, and ethyl carbitol; halogenated hydrocarbons, such as carbon tetrachloride, methylene chloride, trichloroethylene, perchloroethylene, trichloroethane, trichlorofluoromethane, tetrachlorodifluoroethane, and trichlorotrifluoroethane; and the like. Preferably, a mixed solvent of isopropanol and ethanol is used. Here, the organic solvent can be used in combination with water.

The mold-releasing agent solution can be applied to a mold by any common method, such as dipping, spraying, brushing, aerosol spraying, or impregnated fabric coating. Moreover, examples of molding materials to be formed by the mold, to which the mold-releasing agent has been applied, include polyurethane, polycarbonate, epoxy resin, phenol resin, polyimide resin, vinyl chloride resin, and other resins; natural rubber, chloroprene rubber, fluororubber, and other rubbers.

In addition, the perfluorocarbon compound capable of dissolving and carrying a large amount of oxygen can be effectively used as an oxygen transport medium or a storage solution for isolated organs in the form of an emulsion containing the perfluoroalkylethyl phosphonic acid salt (see Patent Document 11).

Examples of the perfluorocarbon compound include perfluorocycloalkanes, such as perfluorocyclohexane and perfluorocyclodecalin; and perfluoroalkylcycloalkanes, such as perfluorotrimethylcyclohexane, perfluoroisopropylcyclohexane, and perfluoroalkyldecalin. The emulsion of the perfluorocarbon compound is formed in the same manner as in the perfluoropolyether oil emulsion.

EXAMPLES

The following describes the present invention with reference to Examples.

Example 1

(1) In a 200-ml reactor equipped with a stirrer and a dropping funnel, 50 g of water heated to 40° C. was charged while keeping the water warm, and 5 g (11.7 mmol) of 2-(perfluorohexyl)ethyl phosphonic acid (CHEMINOX FHP-2-OH, produced by Unimatec Co., Ltd.) was added thereto. Then, 20.5 g (16.9 mmol) of an aqueous ammonia solution with a concentration of 1.4 wt. % was added, and stirring was continued for one hour to perform neutralization reaction. As a result, an aqueous solution of 2-(perfluorohexyl)ethyl phosphonic acid ammonium salt having a pH of 8 (active ingredient concentration: 6.9 wt. %) was obtained [emulsifier aqueous solution I].

The emulsifier aqueous solution I was gradually added with each small amounts to water, and the surface tension of the aqueous solution was measured. As shown by circles (0) in the graph of FIG. 1, the critical micelle concentration [CMC] of the solution was 0.8 wt. %, and the minimum surface tension was 17 mN/m. The surface tension was measured at 20° C. by the maximum bubble method using a dynamic surface tensiometer (produced by SITA).

Meanwhile, when stirring was carried out for one hour without adding an aqueous ammonia solution to 2-(perfluorohexyl)ethyl phosphonic acid, the added 2-(perfluorohexyl) ethyl phosphonic acid was not dissolved in water and was separated. As a result, no aqueous solution was obtained.

(2) In a 1,000-ml reactor equipped with a stirrer and a dropping funnel, 182 g of water heated to 40° C. was charged while keeping the water warm, and 218 g of emulsifier aqueous solution I and 100 g of perfluoropolyether oil represented by the general formula:

$C_3F_7O[CF(CF_3)CF_2O]_mC_2F_5$ (m: 2 to 100)

(BARRIERTA J 25 FLUID, produced by NOK Kluber Co., Ltd.; kinetic viscosity (40° C.): 25 mm$^2$/s) were added thereto (the total amount of the mixture: 500 g). Subsequently, preliminary emulsification was carried out for two minutes using a homogenizer at a rotational speed of 3,000 rpm. Emulsifying treatment was further carried out using a high-pressure homogenizer (produced by Nippon Seiki Co., Ltd.) at a pressure of 600 kgf/cm$^2$ (58.8 MPa), thereby obtaining 485 g (recovery rate: 97%) of perfluoropolyether oil emulsion A (the amount of perfluoroalkylethyl phosphonic acid ammonium salt was 15.0 parts by weight based on 100 parts by weight of perfluoropolyether oil).

The average particle diameter of the obtained perfluoropolyether oil emulsion A was 151 nm. The emulsion A was allowed to stand for one month at room temperature and 40° C., and the average particle diameters then measured were 153 nm and 155 nm, respectively. It was confirmed that the formed emulsion was stable in both cases. The average particle diameter was measured by a dynamic light-scattering method using a particle size distribution analyzer (Microtrac UPA150, produced by Nikkiso Co., Ltd.).

When the amount of water was changed to 385 g, and 15 g of 2-(perfluorohexyl)ethyl phosphonic acid was used in place of the emulsifier aqueous solution I, the mixture immediately underwent liquid-liquid separation, and no emulsion was formed.

Reference Example 1

In Example 1 (1), 5 g of pentadecafluorooctanoic acid ammonium salt (EFTOP EF-204, produced by Jemco Co., Ltd.) was used in place of the of 2-(perfluorohexyl)ethyl phosphonic acid and aqueous ammonia solution, thereby obtaining an aqueous solution of the ammonium salt (active ingredient concentration: 9.1 wt. %) [emulsifier aqueous solution II].

When the surface tension of the emulsifier aqueous solution II was measured in the same manner, the CMC of the solution was 0.8 wt. %, and the minimum surface tension was 18 mN/m, as shown by black squares (■) in the graph of FIG. 1.

Example 2

In Example 1 (2), the same amount (100 g) of perfluoropolyether oil represented by the same general formula (BARRIERTA J 100 FLUID, produced by NOK Kluber Co., Ltd.; kinetic viscosity (40° C.): 95 mm$^2$/s) was used (total amount: 500 g), thereby obtaining 486 g (recovery rate: 97%) of perfluoropolyether oil emulsion B. The average particle diameter of the emulsion B was 131 nm, the average particle diameter after one month at room temperature was 136 nm, and the average particle diameter after one month at 40° C. was 140 nm. Thus, it was confirmed that the formed emulsion was stable.

Example 3

In Example 1 (2), the same amount (100 g) of perfluoropolyether oil represented by the same general formula (BARRIERTA J 400 FLUID, produced by NOK Kluber Co., Ltd.; kinetic viscosity (40° C.): 390 mm$^2$/s) was used (total amount: 500 g), thereby obtaining 485 g (recovery rate: 97%) of perfluoropolyether oil emulsion C. The average particle diameter of the emulsion C was 145 nm, the average particle diameter after one month at room temperature was 146 nm, and the average particle diameter after one month at 40° C. was 150 nm. Thus, it was confirmed that the formed emulsion was relatively stable.

Example 4

In Example 1 (2), the same amount (100 g) of perfluoropolyether oil represented by the same general formula (BARRIERTA J 800 FLUID, produced by NOK Kluber Co., Ltd; kinetic viscosity (40° C.): 800 mm$^2$/s) was used (total amount: 500 g), thereby obtaining 480 g (recovery rate: 96%) of perfluoropolyether oil emulsion D. The average particle diameter of the emulsion D was 155 nm, the average particle diameter after one month at room temperature was 160 nm, and the average particle diameter after one month at 40° C. was 162 nm. Thus, it was confirmed that the formed emulsion was relatively stable.

Example 5

In Example 1 (2), the same amount (100 g) of perfluorodecalin was used in place of the perfluoropolyether oil, thereby obtaining 484 g (recovery rate: 97%) of perfluorodecalin emulsion E. The average particle diameter of the emulsion E was 189 nm, the average particle diameter after one month at room temperature was 190 nm, and the average particle diameter after one month at 40° C. was 200 nm. Thus, it was confirmed that the formed emulsion was stable.

Reference Example 2

In Example 2, 165 g of emulsifier aqueous solution II, which was a pentadecafluorooctanoic acid ammonium salt aqueous solution, was used in place of the emulsifier aqueous solution I, and the amount of water was changed to 235 g (total amount: 500 g), thereby obtaining 482 g (recovery rate: 96%) of perfluoropolyether oil emulsion F. The average particle diameter of the emulsion F was 140 nm, the average particle diameter after one month at room temperature was 143 nm, and the average particle diameter after one month at 40° C. was 145 nm. Thus, the formed emulsion was stable.

Reference Example 3

In Example 5, 165 g of the emulsifier aqueous solution II, which was a pentadecafluorooctanoic acid ammonium salt aqueous solution, was used in place of the emulsifier aqueous solution I, and the amount of water was changed to 235 g (total amount: 500 g), thereby obtaining 483 g (recovery rate: 97%) of perfluorodecalin emulsion G The average particle diameter of the emulsion G was 185 nm, the average particle diameter after one month at room temperature was 182 nm, and the average particle diameter after one month at 40° C. was 196 nm. Thus, the formed emulsion was relatively stable.

Example 6

(1) In Example 1 (1), 1.71 g (16.9 mmol) of triethylamine was used in place of 20.5 g (16.9 mmol) of aqueous ammonia solution with a concentration of 1.4 wt. %, thereby obtaining an aqueous solution of 2-(perfluorohexyl)ethyl phosphonic acid triethylamine salt (active ingredient concentration: 8.9 wt. %) [emulsifier aqueous solution III].

When the critical micelle concentration [CMC] and minimum surface tension of the emulsifier aqueous solution III were measured in the same manner, the results were 1.2 wt. % and 27.7 mN/m, respectively.

(2) In Example 1 (2), the amount of water heated to 40° C. was changed to 231 g, the emulsifier aqueous solution III was used in place of the emulsifier aqueous solution I in an amount of 169 g, and the amount of perfluoropolyether oil (BARRIERTA J 100 FLUID) was changed to 100 g. The type and amount were thus changed (total amount: 500 g), thereby obtaining 483 g (recovery rate: 97%) of perfluoropolyether oil emulsion H.

The average particle diameter of the obtained perfluoropolyether oil emulsion H was 405 nm. Moreover, when the emulsion H was allowed to stand for one month at room temperature and 40° C., precipitation occurred, and separation was observed in both cases.

Example 7

The perfluoropolyether oil emulsion A (2.5 parts by weight) was added, while stirring, to 97.5 parts by weight of ion exchange water for dilution, thereby preparing a mold-releasing agent emulsion.

Using the mold-releasing agent emulsion, mold release test in urethane rubber molding was performed as follows.

An aluminum cup (45 mm in diameter and 50 mm in depth) was used as a mold. After the mold was heated to 80° C., the mold-releasing agent was applied thereto and dried at 80° C. Into the mold to which the mold-releasing agent had been applied, 10 g of a mixture of 100 parts by weight of urethane prepolymer (Coronate 4090, produced by Nippon Polyurethane Industry Co., Ltd.) heated to 80° C. and 12.8 parts by weight of a methylenebis(o-chloroaniline) curing agent (Iharacuamine MT, produced by Ihara Chemical Industry Co., Ltd.) heated to 120° C. was poured, and cured by heating at 120° C. for one hour.

Before curing, a hook was stood in the center of the mold for removing the cured molded product. When the load required to pull the hook to take out the molded product from the mold after curing was measured by a spring scale positioned above the mold, the result was 8 N (mold releasability). Further, when how many times a one-time application of the mold-releasing agent allowed mold releasing at a mold release load of 50 N or less was measured, the result was 9 times (mold release life).

Comparative Example 1

(1) In Example 1 (1), the amount of 2-(perfluorohexyl) ethyl phosphonic acid was changed to 10 g (23.4 mmol), and the amount of aqueous ammonia solution with a concentration of 1.4 wt. % was changed to 40 g (32.9 mmol), thereby obtaining an aqueous solution of the ammonium salt (active ingredient concentration: 10.0 wt. %) [emulsifier aqueous solution IV].

(2) In Example 1 (2), 250 g of emulsifier aqueous solution IV, 5 g of perfluoropolyether oil (BARRIERTA J 100 FLUID), and 245 g of water were used (the total amount of the mixture: 500 g), thereby obtaining 486 g (recovery rate: 97%) of perfluoropolyether oil emulsion I. The average particle diameter of the emulsion I was 61 nm, the average particle diameter after one month at room temperature was 65 nm, and the average particle diameter after one month at 40° C. was 66 nm. Thus, it was confirmed that the formed emulsion was relatively stable.

(3) In Example 7, the same amount (2.5 parts by weight) of perfluoropolyether oil emulsion I was used in place of the perfluoropolyether oil emulsion A, thereby preparing a mold-releasing agent emulsion. Using the mold-releasing agent emulsion, mold release test in urethane rubber molding was performed. The results were such that mold releasability was 20 N, and mold release life was twice.

Examples 8 to 14 and Comparative Example 2 and 3

In Example 7, the type and amount (wt. %) of perfluoropolyether oil emulsion used in the preparation of mold-releasing agent emulsions, and the type (water: ion exchange water, EtOH: ethanol, IPA: isopropanol) and amount (wt. %) of diluent were each changed as shown in the following table. The following table shows the measured results of mold releasability and mold release life, together with the measured results of Example 7.

TABLE

| Example | Emulsion | | Diluent | | | Mold releasability (N) | Mold release life (time) |
|---|---|---|---|---|---|---|---|
| | Type | Amount | Water | EtOH | IPA | | |
| Ex. 7 | A | 2.5 | 97.5 | — | — | 8 | 9 |
| Ex. 8 | B | 2.5 | 97.5 | — | — | 10 | 8 |
| Ex. 9 | B | 1.25 | 98.75 | — | — | 13 | 6 |
| Ex. 10 | B | 0.625 | 99.375 | — | — | 15 | 6 |
| Ex. 11 | B | 2.5 | 82.5 | 15.0 | — | 9 | 7 |
| Ex. 12 | B | 2.5 | 82.5 | 12.0 | 3.0 | 8 | 10 |
| Ex. 13 | C | 2.5 | 97.5 | — | — | 8 | 9 |
| Ex. 14 | D | 2.5 | 97.5 | — | — | 7 | 8 |
| Comp. Ex. 2 | F | 2.5 | 97.5 | — | — | 12 | 5 |
| Comp. Ex. 3 | G | 2.5 | 97.5 | — | — | 20 | 2 |

Comparative Example 4

In Example 7, mold releasability and mold release life were measured without applying the mold-releasing agent emulsion. The results were such that the mold releasability could not be measured because the molded product was not removed from the mold, and the mold release life was therefore 0 times.

The invention claimed is:

1. An aqueous emulsion comprising, as an emulsifier, 0.01 to 30 parts by weight of a perfluoroalkylethyl phosphonic acid salt represented by the general formula:

$C_nF_{2n+1}CH_2CH_2P(O)(OM^1)(OM^2)$ [III]

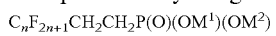

wherein $M^1$ is a hydrogen atom or unsubstituted ammonium salt, $M^2$ is an unsubstituted ammonium salt, and n is an integer of 1 to 6, based on 100 parts by weight of a perfluoropolyether oil represented by the general formula:

$RfO[CF(CF_3)CF_2O]_mRf'$ [I]

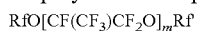

wherein Rf and Rf' are perfluoro-lower alkyl groups having 1 to 5 carbon atoms and m is an integer of 2 to 200, said perfluoroalkylethyl phosphonic acid salt and perfluoropolyether oil being dispersed in water or an aqueous solution to form the aqueous emulsion.

2. The aqueous emulsion according to claim 1, wherein the emulsifier comprises an aqueous solution or an organic solvent solution.

3. A surface-treating agent comprising an aqueous solution in which the perfluoropolyether oil emulsion according to claim 1 is further diluted with an aqueous medium.

4. A water- and oil-repellent, an anti-adhesion agent, a transfer inhibitor, or a mold-releasing agent which comprises the surface-treating agent according to claim 3.

5. A mold-releasing agent that comprises the surface-treating agent according to claim 4, that is applied to a forming mold.

6. The aqueous emulsion according to claim 1, wherein the emulsifier is further diluted with an aqueous medium so as to have a solid matters content of 0.01 to 30 wt. %.

* * * * *